United States Patent [19]

Charm

[11] Patent Number: 4,839,142
[45] Date of Patent: Jun. 13, 1989

[54] HIGH TEMPERATURE, SHORT TIME HEATING SYSTEM AND METHOD OF STERILIZING OR PASTEURIZING HEAT SENSITIVE BIOLOGICAL FLUIDS

[76] Inventor: Stanley E. Charm, 21 Concolor Ave., Newton, Mass. 02158

[21] Appl. No.: 71,733

[22] Filed: Jul. 8, 1987

Related U.S. Application Data

[63] Continuation-in-part of Ser. No. 782,019, Sep. 30, 1985, abandoned.

[51] Int. Cl.$^4$ ............................ A61L 2/12; C07K 3/12
[52] U.S. Cl. ........................... 422/21; 426/241; 426/521; 426/522; 435/2; 530/363; 530/380; 530/383
[58] Field of Search .............. 422/21, 307; 530/363, 530/380, 383; 426/234, 241, 243, 521, 522; 219/10.55 R, 10.55 A, 10.55 F, 10.55 M; 210/748, 764, 774, 177, 181, 182, 96.2, 929; 435/2

[56] References Cited

U.S. PATENT DOCUMENTS

| | | | |
|---|---|---|---|
| 1,863,222 | 6/1932 | Hoermann . | |
| 2,333,842 | 11/1943 | Cascio et al. | 250/49.5 |
| 3,256,101 | 6/1966 | Arns | 426/241 |
| 3,296,122 | 1/1967 | Karassir et al. | 210/181 |
| 3,439,510 | 4/1969 | Gray | 62/78 |
| 3,492,212 | 1/1970 | Searcy | 204/160.1 |
| 3,494,724 | 2/1970 | Gray . | |
| 3,535,482 | 10/1970 | Kluck | 219/10.55 |
| 3,579,631 | 5/1971 | Stewart, Jr. et al. | 426/521 |
| 3,623,894 | 11/1971 | Lund | 426/522 |
| 3,660,234 | 5/1972 | Gray | 424/89 |
| 3,676,058 | 7/1972 | Gray . | |
| 3,706,631 | 12/1972 | Falk . | |
| 3,764,009 | 10/1973 | Watt | 210/177 |
| 3,809,845 | 5/1974 | Stenstrom | 422/21 |
| 3,934,042 | 1/1976 | DeStoutz | 426/522 |
| 4,251,437 | 2/1981 | Rasmussen et al. . | |
| 4,260,490 | 4/1981 | Moss et al. | 210/96.1 |
| 4,366,051 | 12/1982 | Fischel | 210/181 |
| 4,393,088 | 7/1983 | Matsusaka | 426/234 |
| 4,395,397 | 7/1983 | Shapiro | 424/101 |
| 4,613,501 | 9/1986 | Horowitz | 435/238 X |
| 4,720,385 | 1/1988 | Lembach | 530/380 X |
| 4,727,027 | 2/1988 | Wiesrhahn et al. | 530/380 X |

*Primary Examiner*—Michael S. Marcus
*Assistant Examiner*—Jill Johnstoz
*Attorney, Agent, or Firm*—Richard P. Crowley

[57] ABSTRACT

A high temperature, short time heating system and method for the pasteurization and/or sterilization of heat sensitive biological fluids, which method comprises: adding a dielectric enhancing additive to the biological fluid; subjecting the biological fluid to microwave energy to heat rapidly the biological fluid for a short time period to a pasteurizing or sterilization temperature; cooling the biological fluid; optionally removing the dielectric enhancing additive; and recovering an aseptic biological fluid.

21 Claims, 1 Drawing Sheet

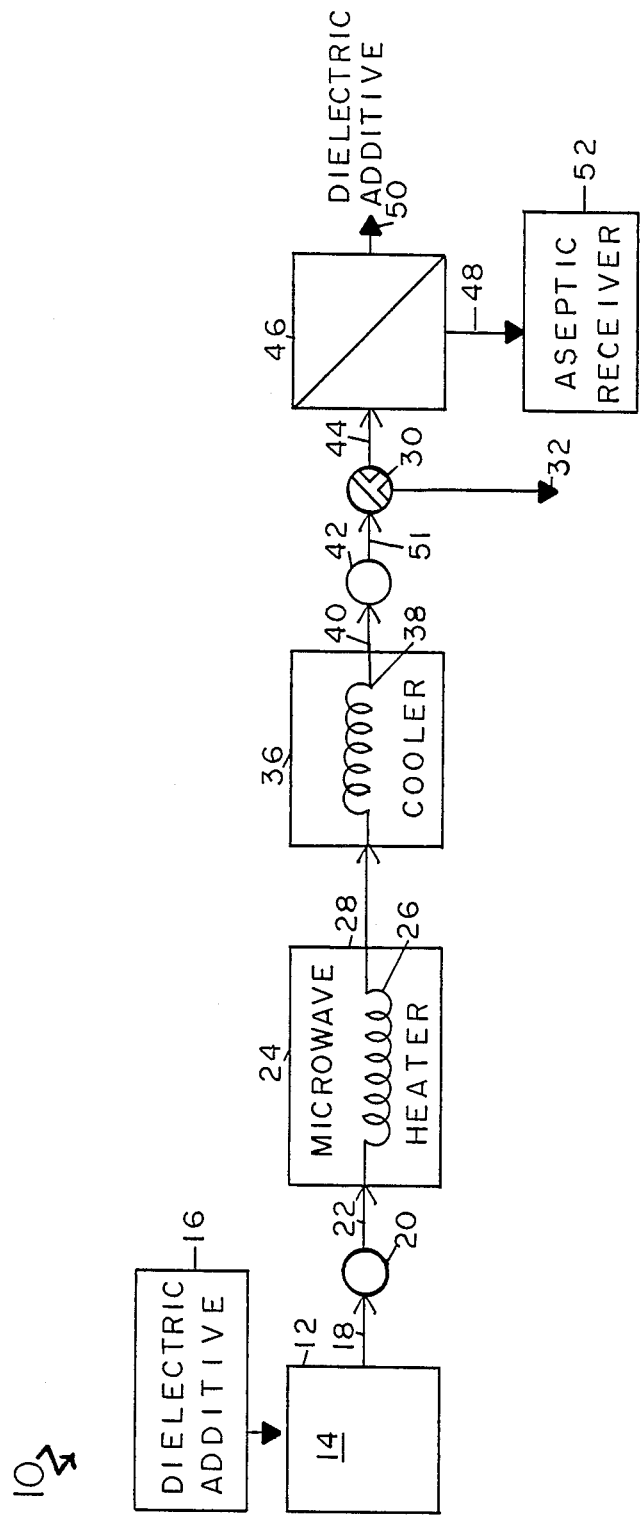

HIGH TEMPERATURE, SHORT TIME HEATING SYSTEM AND METHOD OF STERILIZING OR PASTEURIZING HEAT SENSITIVE BIOLOGICAL FLUIDS

Reference to Prior Applications

This application is a continuation-in-part application of U.S. Ser. No. 782,019, filed Sept. 30, 1985, now abandoned.

DESCRIPTION

Background of the Invention

It is often desirable, particularly in the food industry, to preserve heat sensitive foods, such as milk or goods with delicate flavor components, by heating such heat sensitive foods to high temperatures for very short periods of time, as in pasteurization and sterilization of food products. However, many such systems are available only for relatively large scale food productions and do not permit small scale laboratory productions or experiments with valuable, low volume material, such as heat sensitive biological fluids or suspensions, used in the laboratory, such as fermentation media, vaccines, liposomes and the cell culture media.

Further, it is often desirable to sterilize biological fluids or suspensions, such as plasma or protein-containing fluids, to destroy selected pathogenic organisms, such as infectious agents like a virus or other agent compound substantially of protein and nucleic acids, without destroying or substantially altering other microorganisms or precipitating or destroying other proteinaceous matter material. For example, it is desirable to destroy selectively virus and virus-type agents from blood plasma without clotting, clouding, aggregating, coagulating, precipitating or biologically altering the plasma in the process.

Therefore, it is desirable to provide for a continuous, fast, heat processing apparatus and a method for the high temperature, short time heating to provide sterilization or pasteurization of heat sensitive biological fluids and suspensions, including body fluids, particularly for use with low volume biological fluids and for small scale laboratory use.

Summary of the Invention

The invention relates to a heat processing apparatus and system and to a method for the high temperature, short time pasteurization for destruction of viruses and/or sterilization of heat sensitive biological fluids. In particular, the invention concerns a microwave-based heat processing system and a method for the high temperature, short time heating of biological fluids employing microwave energy with high dielectric biological fluids.

The present invention permits the continuous, rapid heating of biological fluids so as to effect sterilization or pasteurization without destroying or substantially altering biological activity, and is particularly useful for, but not limited to, small scale laboratory production or experiments with valuable, low volume biological fluids or materials and the selective destruction of infectious agents, like viruses and virus-type agents, from body fluids, such as blood plasma.

The method of the invention comprises employing microwave energy, such as derived from a microwave oven or generator, as a microwave source to heat a high dielectric biological fluid rapidly at a very high rate, for example 25° C. to 8000° C. per second, typically 50° C. per second or more, e.g. 50° C. to 4000° C. per second, to a defined sterilization temperature, for example of 143° C. or more, or to a defined pasteurization temperature, for example of 60° C. to 80° C. or more, and held at that temperature for about 0.05 seconds or less. The method of the invention comprises the subjecting of a heat sensitive biological fluid, such as, but not limited to, blood plasma containing a virus, to microwave energy, typically by the employment of a commercial or industrial microwave generator of 500 to 10,000 watt power which contains a microwave permeable zone, e.g. of plastic or glass tubing therein, through which the biological solution is circulated for a selected period of time to achieve sterilization or pasteurization temperatures. For higher flow rates, microwave generators with higher power inputs are used.

In one embodiment, since the heating time in a microwave source depends on the dielectric constant of the biological fluid, a dielectric constant enhancing additive is typically employed and added to the heat sensitive biological fluid to adjust the dielectric constant to provide the short heat time period. The enhancing additive must be dissolved in the biological fluid. The additive is of a type and added in an amount sufficient to provide for enhanced dielectric constant of the fluid, so that the biological fluid may be rapidly heated by the microwave energy in a short time period. The dielectric constant additive should not affect the desired essential nature or quality of the biological fluid to which it is added, i.e. should be biologically inert. The additive may comprise a high dielectric salt or salt solution, and typically an inorganic metal or ionic salt, such as an alkali or alkaline earth salt, with sodium chloride, one preferred additive for blood plasma. Typically, the additive is added to the biological fluids in an aqueous solution. Where the biological fluid already has a high dielectric constant, e.g. over 100, then depending on the heating time period desired, an additive need not be employed.

The biological fluids to which the dielectric constant enhancing additive is added are circulated by pumping, typically through plastic or glass tubing extending through the microwave oven or waveguide, so that the fluid may be rapidly heated to the selected sterilization or pasteurization temperature. The heated biological fluid with the additive is then cooled, and optionally, the dielectric additive is then removed and an aseptic biological fluid recovered.

The method may be used to sterilize a wide variety of biological fluids, such as microbiological media, tissue culture media, suspensions that cannot be sterilized employing ultrafiltration, such as liposomes or collagens, vaccines, mother's milk, fermentation media and cell culture media. It may also be used to pasteurize or sterilize blood plasma (whole plasma or serum) and blood plasma products containing Factors VIII and IX, and to destroy selectively agents likes viruses and microplasma, such as hepatitis, AIDS and the like. The system is designed to accommodate flow rates generally of from about 3 liters per hour or more, e.g. 3 to 25 liters per hour with a hold-up volume of about 0.5 liters or less.

The system employs a microwave power source and the necessary instrumentation to maintain sufficient back-up pressure to permit a temperature of the fluid in the oven, e.g. of 160° C., that is, selected sterilization or pasteurization temperature or such other predetermined temperature. Residence times of 2 seconds or less at the sterilization temperature of 143° C. are typically sufficient to achieve sterility as defined by the 12 log cycle reductions of a heat resistant microorganism, such as Cl botulinum.

Since the heating-up time of the fluid in the microwave oven depends on the dielectric constant of the fluid being heated, the dielectric constant enhancing additive is added in various amounts as required, such as sodium chloride or other inert, pharmaceutically inactive salt or salt solutions, more typically as a saline solution. While the amount of the dielectric constant enhancing additive may vary depending on the dielectric constant of the original biological fluid, generally from about 0.1 to 10 percent or more by weight of the fluid of a salt may be added, 0.5 to 4.0 percent, and even more particularly 0.05 to about 1.5 percent, is often sufficient to enable rapid sterilization in a commercial microwave oven or industrial microwave generator. Excessive quantities of the dielectric constant enhancing additive should be avoided, since optionally the additive should be removed from the sterilized biological fluid. The biological fluid with the additive may vary in dielectric constant depending on the desired temperature to be reached, but generally the biological fluid with the additive should have a dielectric constant of at least that of water, such as from about 90 to 300, such as about 100 to 200.

The size of the tubing in the microwave heater, usually in coiled or serpentine form, employed must hold up sufficient volume within the microwave chamber so that sufficient microwave energy will be absorbed to prevent burning out of the magnetron tubes in the microwave generator. A higher dielectric constant biological fluid will of course require a smaller hold-up volume than a lower dielectric constant material. Therefore, where adjustment of a dielectric constant cannot be entirely made employing a dielectric constant enhancing additive, varying tubing size for circulating the biological fluids through the microwave oven should be used to accommodate different ranges of dielectric constant fluids.

The biological fluid to which the dielectric constant enhancing additive has been added is generally circulated through tubing in the microwave heater by a pump. Also, a back pressure valve is typically employed after the cooler to prevent flashing of the fluid or vaporization of the heated biological fluid, and a divert valve is employed after the cooling mechanism so that any biological fluid which does not reach the necessary selected sterilization temperature may be diverted. Generally, such biological fluid is not recycled, but discarded, since high temperature heating of the biological fluid may alter the fluid. However, where such alteration does not affect the biological fluid, any biological fluid diverted by the divert valve and which is not adversely affected by reheating may be recycled as a biological fluid source for reheating in the microwave oven. Also, generally where the dielectric constant enhancing agent is added, it is desirable to remove such enhancing agent from the sterilized biological fluid under aseptic conditions, such as by the employment of ultrafiltration, dialysis or chromatography columns or other salt separation techniques. Thus, the dielectric constant enhancing agent, where applicable, should also be selected for easy or effective removal or separation from the sterilized biological fluid prior to recovery of the biological fluid in an aseptic receiver. Optionally, certain products, such as blood clotting factors, may be removed from blood plasma after the short time heating process and the removal of the dielectric enhancer, e.g. salt, may be unnecessary.

The heat processing system of the invention comprises: a source of biological fluid to be heated or sterilized; means to provide for the addition of a sufficient amount of a dielectric constant enhancing agent to the biological fluid; means to circulate, such as by pumping, the biological fluid with the additive to adjust the dielectric constant to be required to obtain the rapid heating to the selected temperature during the time of exposure to the microwave energy through a microwave permeable container, such as tubing, at a desired length and diameter through a microwave source, such as a commercial microwave oven, for a defined hold-up time; a cooling means, such as a cooler, to cool the heated processed biological fluid to a lower temperature, such as 20° C. or lower, a back pressure valve means to prevent the vaporization of the heat sterilized material; optionally, but preferably, a divert valve means so that the material that is not at the desired sterilizing or pasteurizing temperatures may be be diverted; optional separating means to remove the dielectric constant enhancing agent from the sterilized biological fluid under sterile conditions; and an aseptic receiver to receive the short time, heat sterilized biological fluid. Optionally, the biological fluid diverted may be recycled to the biological fluid source, and of course, the inert dielectric constant enhancing agent also may be recycled for further use with biological fluid after removal.

The invention will be described for the purposes of illustration only in connection with certain embodiments; however, it is recognized that various changes, additions and improvements may be made in the invention by those persons skilled in the art, without departing from the spirit and scope of the invention.

BRIEF DESCRIPTION OF THE DRAWING

The drawing is a schematic, illustrative drawing of a heat processing system employing the method of the invention.

DESCRIPTION OF THE EMBODIMENTS

The drawing shows a heat processing system 10 comprising a container 12 containing a heat sensitive biological fluid 14 and a source of a dielectric additive 16, such as a sodium chloride solution, which is added to the heat sensitive biological fluid 14. The biological fluid 14 with the dielectric additive is then introduced through line 18 through pump 20 and line 22 into a microwave heater 24 wherein a defined volume of the biological fluid is present in the plastic tubing 26 and subject to microwave energy wherein the biological fluid now at a high dielectric constant is heated at a high rate, 50° C. per second or more, for about 3.0 seconds or less, to 160° C. The heated fluid is then withdrawn through line 28. The fluid is held at the high temperature for 0.1 seconds or less in line 28. The biological fluid is then introduced into a metal tube in a cooler 36 where it is cooled to room temperature, for example 20° C. or below, and then introduced through line 40 through a back pressure valve 42 which prevents the vaporization of the heated fluid. The heated fluid is then withdrawn through line 51 through a divert three-way valve (off-on-divert) 30. If the biological fluid does not reach the heat sterilizing or pasteurizing temperature, the biological fluid is diverted through line 32 and discarded. The heated fluid may then be introduced through line 44 into a separator 46, such as a dialysis unit or chromatography column, ultrafiltration or other separation means, and all or some of the added dielectric additive is then removed through line 50 and the sterilized biological fluid is removed through line 48 into an aseptic receiver 52 for laboratory, experimental or other use.

EXAMPLE 1

Certain tests were conducted employing saline solutions of various weight percent salt with an initial temperature of about 27° C. and a resulting cooled temperature of about 4° C. employing the apparatus as described in the drawings with the test results as set forth in the accompanying table.

TABLE I

| | Saline Solution | | | |
|---|---|---|---|---|
| Weight Percent Salt | Heating Time (seconds) to 143° C. | Holding Time (seconds) at 143° C. | Cooling Time (seconds) | Flow Rate L/hr |
| 0.5 | 16 | 0.5 | 2.5 | 3.6 |
| 0.9 | 6 | 0.5 | 2.5 | 3.3 |
| 1.5 | 5 | 0.5 | 2.5 | 3.3 |
| 4.0 | 3.5 | 0.15 | 2.5 | 3.3 |

As illustrated, the saline solutions of 0.9 and 1.5 percent, in contrast to the lower dielectric constant saline solution of 0.5 percent, provide for a very rapid increase in temperature in less than 6 seconds to the sterilization time and temperature of 143° C. and for a holding time of one-half of a second, all with substantially the same flow rates. The use of a 4 percent saline solution provides for a more rapid temperature rise and short time, 0.15 seconds, at a sterilization temperature of 143° C. to 144° C.

EXAMPLE 2

A heat sensitive biological fluid comprising blood plasma to which has been added 4 weight percent sodium chloride was processed in the apparatus of the drawing, but without the removal of the salt, with the results shown in Table II.

TABLE II

| | 4 Percent Salt Blood Plasma Fluid | | | |
|---|---|---|---|---|
| Final Temperature (°C.) | Heating Time (seconds) | Holding Time (seconds) | Cooling Time (seconds) | Remarks |
| 68 | 1.5 | 0.05 | 0.9 | No clotting |
| 71 | 1.75 | 0.06 | 1.1 | No clotting |
| 76 | 1.9 | 0.07 | 1.2 | No clotting |
| 81 | 2.1 | 0.07 | 1.3 | Clotting |

Flow Rate: 3.3 L/hr
Microwave Oven Power: 700 watts
Hold-up Volume in Microwave: 40 ml In Example 2, there was no change in albumin, globins or Factors VIII and IX in comparison to an unprocessed control sample. Example 2 demonstrates that heat sensitive blood plasma containing pathogenic viruses, such as hepatitis B or AIDS, may be pasteurized with the destruction of the viruses by the rapid high temperature microwave heating method. As illustrated, the pasteurization holding time with the addition of the dielectric additive is very short, 0.05 to 0.07 seconds, to provide heating without affecting clotting factors unless the heating time is more than 1.9 seconds with a holding time of 0.07 seconds.

EXAMPLE 3

Blood plasma has been processed in the prior art at temperatures of 59° C. for a time period of 12 hours in an attempt to destroy viruses and yet to preserve the blood clotting factors of the blood plasma, e.g. Factors VIII and IX; however, the hepatitis B virus and other agents can survive this process. Further, the process is time consuming. It has been found possible to achieve high temperatures, e.g. 75° C. or more, for short time periods, e.g. for 0.5 seconds or less, such as 0.05 seconds, employing microwave energy and still preserve the blood clotting factors in the blood plasma while destroying by the short heating time infectious agents, such as viruses. By achieving temperatures and times in the range of 75° C. for 0.05 seconds, it is possible to preserve Factors VIII and IX in blood plasma with 4 percent salt in the plasma and to destroy viruses in the plasma.

In determining the amount of dielectric additive necessary to be added, a measure of the dielectric constant may be obtained by passing the liquid at a rate of 8.35 liters/hour through 28 feet of 1/16" I.D. tubing spaced throughout the volume of the microwave heater and allowing the system to come to a steady state. The liquid residence time in microwave is 7.04 seconds.

TABLE III

| Material | Initial Temperature (°C.) | Final Temperature (°C.) | Difference (°C.) | Percent Change From Water |
|---|---|---|---|---|
| Water | 25.6 | 62.2 | 36.6 | — |
| 0.5% Salt | 25.0 | 72.8 | 47.8 | +30.6 |
| 1.0% Salt | 22.8 | 78.3 | 55.5 | +51.6 |
| 2.0% Salt | 23.9 | 85.0 | 61.1 | +66.9 |
| 4.0% Salt | 25.0 | 91.7 | 66.7 | +82.2 |
| 10.0% Salt | 28.3 | 98.3 | 70.0 | +91.3 |
| 20.0% Salt | 22.2 | 95.0 | 72.7 | +98.6 |

As illustrated by the test data in Table III, the increase in temperature rise is associated with an increase in dielectric constant (water having a dielectric constant of about 69 and 4 percent salt solutions about 126).

EXAMPLE 4

A heat sensitive biological fluid comprising DMEM tissue culture media with 10% fetal bovine serum had T4 coliphage added. T4 coliphage is a bacterial virus. The media was processed (pasteurized) in the apparatus of the drawing. No salt was added or removed because the DMEM media had a high dielectric constant due to ionic material originally in the DMEM.

TABLE IV

| Initial Temperature (°C.) | Heating Time (seconds) | Holding Time (seconds) | Cooling Time (seconds) | Final Temperature (°C.) | Concentration of T4 Coliphage (units/ml) | Comments |
|---|---|---|---|---|---|---|
| 20 | 1.4 | 0.01 | 2.55 | 61 | $4.3 \times 10^{10}$ | No reduction of phage |
| 20 | 1.4 | 0.01 | 2.55 | 78 | $3.4 \times 10^{10}$ | Slight reduction of phage |

TABLE IV-continued

| Initial Temperature (°C.) | Heating Time (seconds) | Holding Time (seconds) | Cooling Time (seconds) | Final Temperature (°C.) | Concentration of T4 Coliphage (units/ml) | Comments |
|---|---|---|---|---|---|---|
| 20 | 1.4 | 0.01 | 2.55 | 93 | None | All T4 Coliphage Destroyed |

Initial concentration of T4 Coliage = $1.7 \times 10^9$ units/ml

The biological solution was tested for presence of T4 coliphage and for concentration of protein in the solution. At 93° C., all the T4 coliphage is destroyed, and the biological fluid retains biologically active proteins.

EXAMPLE 5

A solution of Staphylococcus aureus bacteria suspended and grown is a fermentation broth of yeast extract, casein hydrolysate and glucose which was processed (sterilized) in the apparatus of the drawing.

TABLE V

| Initial Temperature (°C.) | Heating Time (seconds) | Heating Temperature (°C.) | Holding Time (seconds) | Cooling Time (seconds) | Sterile | Protein A Binding To $I_gG$ Antibodies |
|---|---|---|---|---|---|---|
| *5 | 2.8 | 160 | 0.016 | 3.2 | Yes | Greater than 2.5 mg/10% solution |
| **5 | 0 | 0 | 0 | 0 | Yes | (0.8 to 1.8 mg)/10% solution |

*Samples were collected aseptically and tested for sterility and Protein A activity.
**Previous method of sterilization by chemical inactivation.
This sample not heated at all.

These experiments indicate the sterlization by the apparatus is more effective than chemical sterilization in this application.

EXAMPLE 6

An artificial blood component consisting of hemoglobin encase in liposome vesicles was suspended in 0.9% weight/volume sodium chloride solution. The solution was processed in the apparatus of the drawing.

TABLE VI

| Initial Temperature | 4° C. |
|---|---|
| Heating Time | 1.4 seconds |
| Holding Time | 0.008 seconds |
| Cooling Time | 2.55 seconds |

The solution was tested and found the integrity of the hemoglobin protein was maintained.

EXAMPLE 7

A different higher heating rate was obtained by using an industrial microwave source to heat the biological solutions. This system reduces the length of tubing inside the microwave field therefore increasing the heating rate of the fluid. The system was tested using different salt water solutions.

TABLE VII

| Solution | Rate (°C./second) | Temperature In (°C.) | Temperature Out (°C.) | Flow (L/hr) | Heating |
|---|---|---|---|---|---|
| .9% NaCl | 23 | 140 | 25.2 | 3046 | |
| .1% NaCl | 24 | 170 | 42 | 6335 | |
| Tap Water | 35 | 125 | 41.7 | 3877 | |

Length of tubing in microwave = 3 cm

With the industrial microwave generator it was not necessary to change the length of tubing in the heating chamber. The dielectric constant change in solution is compensated for by a tuning circuit in the microwave chamber.

What is claimed is:

1. A method for the high temperature, short time heating of a heat-sensitive biological fluid comprising proteinaceous material and a pathogenic organism agent, which method comprises:
   (a) rapidly heating the heat-sensitive biological fluid, having a dielectric constant of over about 90 at a rate of over about 25° C. per second for a heating time period to a preselected heating temperature by the employment of microwave heating energy to provide a heated biological fluid;
   (b) holding the said heated biological fluid at the heating preselected temperature for a holding time period of up to about two seconds;
   (c) rapidly cooling the heated biological fluid to a preselected lower temperature for a cooling time period to provide a cooled biological fluid; and
   (d) circulating the heated biological fluid while rapidly heating, holding and rapidly cooling the biological fluid; wherein
   (e) the heating, holding and cooling time periods are sufficiently short and the preselected heating temperature and the lower temperature are sufficient not to effect the desirable properties of the proteinaceous material of the heat-sensitive biological fluid, but sufficient in time periods and selected temperature for at least the partial destruction of said pathogenic organism agent in the biological fluid.

2. The method of claim 1 wherein said dielectric constant of said heat-sensitive biological fluid is obtained by adding a dielectric enhancing additive prior to said heating step.

3. The method of claim 2 which further includes removing at least a portion of the dielectric enhancing additive from the cooled biological fluid.

4. The method of claim 1 wherein said dielectric constant of said heat-sensitive biological fluid is obtained by adding a dielectric enhancing additive of an ionic salt in an amount of about 0.1% to 10% by weight prior to said heating step.

5. The method of claim 1 wherein said preselected heating temperature is at least about 60° C. and said holding time period is at most about 0.05 seconds.

6. The method of claim 1 wherein said preselected heating temperature is at least about 143° C. and said holding time period is at most about 0.05 seconds.

7. The method of claim 1 wherein the heat-sensitive biological fluid is selected from the group consisting of body fluids, mother's milk, vaccines, fermentation broths and microbiological and cell media.

8. The method of claim 1 wherein said heating of the biological fluid at a rate of about 50° C. to 8,000° C. per second.

9. The method of claim 1 wherein the biological fluid comprises blood plasma or serum and which includes heating the blood plasma or serum to a selected temperature of over about 75° C. and said holding time period is at most about 0.05 seconds.

10. The method of claim 1 wherein said cooler temperature is at most about 20° C.

11. The method of claim 1 which includes circulating the said biological fluid at a flow rate of about 3 to 25 liters per hour with a hold-up volume of less than about 0.5 liters.

12. A method for the high temperature, short time heating of a blood plasma or serum to destroy an infectious agent therein, which method comprises:
   (a) adding a dielectric salt additive to the blood plasma or serum to increase the dielectric constant of the blood plasma or serum to provide a dielectric constant of said blood plasma or serum of about 90 to 300; and
   (b) rapidly heating the dielectric salt-containing blood plasma or serum to a selected temperature of about 60° C. or more for a holding period of time of less than about 0.1 seconds by microwave heating energy to substantially destroy the agent without substantially altering albumin or blood clotting Factors VIII and IX of the blood plasma or serum.

13. The method of claim 12 wherein includes heating the blood plasma or serum at a rate of about 50° C. to 4000° C. per second.

14. The method of claim 12 wherein said holding time period should be less than about 0.05 seconds and wherein said method further includes rapidly cooling the blood plasma or serum after said heating step.

15. The method of claim 14 wherein said selected temperature is at least 75° C. to provide a sterilized blood plasma or serum.

16. The method of claim 12 which further includes separating from the blood plasma or serum at least a part of the dielectric salt subsequent to said heating.

17. The method of claim 1 wherein the infectious agent comprises a virus.

18. A high temperature, short time heat process system for the rapid heating, holding and cooling of a heat-sensitive biological fluid to destroy undesirable biological agents therein without substantial alteration of desirable proteinaceous components or properties of the biological fluid, which system comprises:
   (a) a source of heat-sensitive biological fluid to be heated;
   (b) a source of dielectric enhancing additive for addition to the biological fluid in an amount sufficient to increase the dielectric constant of said biological fluid to a dielectric constant of over about 90;
   (c) microwave heating energy means to heat rapidly for a heating time period said biological fluid at a rate of about 25° C. to 8,000° C. per second to a preselected heating temperature for a holding time period of up to about two seconds;
   (d) cooling means to cool rapidly the heated biological fluid to a preselected cooler temperature in a cooling time period to provide a cooled biological fluid;
   (e) circulating means within the microwave heating energy means and cooling means to permit the flow of said biological fluid through said microwave heating energy means in a microwave heating relationship and through the cooling means in a cooling relationship;
   (f) pump means to pump said biological fluid through said circulating means; and
   (g) means to recover the cooled biological fluid.

19. The system of claim 18 which further includes a means to separate from the cooled biological fluid at least part of the dielectric enhancing additive.

20. The system of the claim 18 which includes a divert valve means to provide for the diversion of biological fluid circulated through the circulating means and microwave heating energy means in the event the biological fluid has not reached the preselected temperature for the holding time period.

21. The system of claim 18 which includes a back pressure valve means to prevent the vaporization in the system of the heated biological fluid.

* * * * *